United States Patent
Mohr et al.

(10) Patent No.: US 10,062,167 B2
(45) Date of Patent: Aug. 28, 2018

(54) ESTIMATED LOCAL RIGID REGIONS FROM DENSE DEFORMATION IN SUBTRACTION

(71) Applicant: Toshiba Medical Systems Corporation, Otawara-shi (JP)

(72) Inventors: Brian Mohr, Edinburgh (GB); James Matthews, Edinburgh (GB); Marco Razeto, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/460,662

(22) Filed: Aug. 15, 2014

(65) Prior Publication Data

US 2016/0048961 A1    Feb. 18, 2016

(51) Int. Cl.
G06K 9/00 (2006.01)
G06T 7/00 (2017.01)
A61B 6/00 (2006.01)
G06T 7/30 (2017.01)
G06T 7/11 (2017.01)

(52) U.S. Cl.
CPC ............ *G06T 7/0024* (2013.01); *A61B 6/481* (2013.01); *A61B 6/505* (2013.01); *A61B 6/507* (2013.01); *A61B 6/5205* (2013.01); *G06T 7/11* (2017.01); *G06T 7/30* (2017.01); *G06T 2207/10081* (2013.01); *G06T 2207/30008* (2013.01)

(58) Field of Classification Search
None
See application file for complete search history.

(56) References Cited

U.S. PATENT DOCUMENTS

| 5,359,513 | A | 10/1994 | Kano et al. | |
|---|---|---|---|---|
| 7,477,770 | B2 * | 1/2009 | Wehrli | G01N 24/08 378/21 |
| 7,689,265 | B2 * | 3/2010 | Shen | G06K 9/38 382/128 |
| 7,920,730 | B2 * | 4/2011 | Jerebko | G06T 7/0012 382/128 |
| 2003/0233039 | A1 * | 12/2003 | Shao | G06T 7/0038 600/407 |
| 2006/0002630 | A1 * | 1/2006 | Fu | G06K 9/32 382/294 |
| 2006/0034500 | A1 * | 2/2006 | Quist | G06T 7/33 382/130 |

(Continued)

OTHER PUBLICATIONS

Barry A. Cipra, "An Introduction to the Ising Model", American Mathematical Monthly, 94.10 (1987), pp. 937-959.

(Continued)

*Primary Examiner* — Matthew Bella
*Assistant Examiner* — Jose M Torres
(74) *Attorney, Agent, or Firm* — Oblon, McClelland, Maier & Neustadt, L.L.P.

(57) ABSTRACT

A medical image data processing apparatus comprises a registration unit configured to perform a non-rigid registration of a first set of medical image data and a second set of medical image data thereby to determine a deformation field, and a region identification unit configured to identify at least one region for which the deformation field is approximately homogeneous, and, for at least part of at least one identified region, to obtain a substantially homogeneous approximation of the deformation field.

19 Claims, 4 Drawing Sheets

(56) References Cited

U.S. PATENT DOCUMENTS

| | | | |
|---|---|---|---|
| 2008/0049999 A1* | 2/2008 | Jerebko | G06T 7/0012 382/128 |
| 2009/0226060 A1 | 9/2009 | Gering et al. | |
| 2011/0015520 A1 | 1/2011 | Meetz et al. | |
| 2011/0158494 A1* | 6/2011 | Bar-Shalev | A61B 6/032 382/131 |
| 2011/0317898 A1* | 12/2011 | Shi | G06T 7/0024 382/131 |
| 2013/0004043 A1* | 1/2013 | Ross | G06T 7/0016 382/131 |
| 2013/0182925 A1* | 7/2013 | Razeto | A61B 6/03 382/131 |

OTHER PUBLICATIONS

Stan Z. Li, "Markov Random Field Modelling in Image Analysis", Springer, (2009), ISBN 978-1-84800-278-4, pp. 31-33.

Alexander McKenzie, et al., "Vector Field Analysis and Visualization through through Variational Clustering" IEEE VGTC Symposium of Visualization 2005, Jun. 2005, pp. 1-7.

Edgar R. Arce-Santana, et al., "Image registration using Markov random coefficient and geometric transformation fields" Pattern Recognition, vol. 42, No. 8, Aug. 2009, pp. 1660-1671 and cover page.

Zoltan Kato, et al., "A Markov random field image segmentation model for color textured images" Image and Vision Computing, vol. 24, No. 10, Oct. 2006, pp. 1103-1114.

Mattias P. Heinrich, et al., "Globally Optimal Deformable Registration on a Minimum Spanning Tree using Dense Displacement Sampling" Med Image Comput Comput Assist Interv., 2012, vol. 15, No. 3, 8 pages.

Pedro Augusto Gondim Teixeira, et al, "Bone Marrow Edema Pattern Identification in Patients With Lytic Bone Lesions Using Digital Subtraction Angiography-Like Bone Subtraction on Large-Area Detector Computed Tomography" Investigative Radiology, vol. 49, No. 3, Mar. 2014, pp. 156-164.

Jim Piper, et al., "Objective Evaluation of the Correction by Non-Rigid Registration of Abdominal Organ Motion in Low-Dose 4D Dynamic Contrast-Enhanced CT" Physics in Medicine and Biology, vol. 57, No. 6, 2012, 17 pages.

W. Lenz (Rostock), "Beitrage zum Verstandnis der magnetischen Eigenschaften in festen Körpern" Physikalische Zeitschrift, vol. 21, 1920, 2 pages.

Y. Hu, et al., "Simulated annealing and iterated conditional modes with selective and confidence enhanced update schemes" Fifth Annual IEEE Symposium on Computer-Based Medical Systems, 1992, pp. 257-264.

* cited by examiner

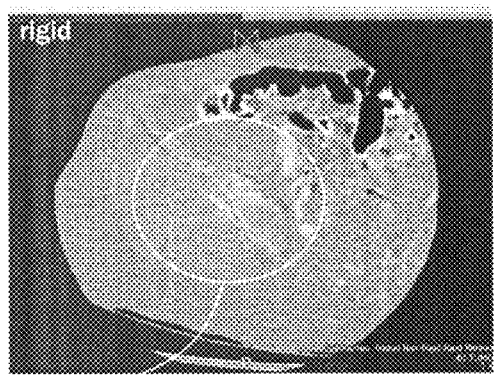 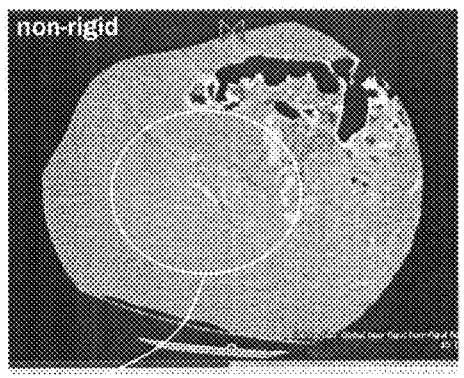
Fig. 3a  Fig. 3b
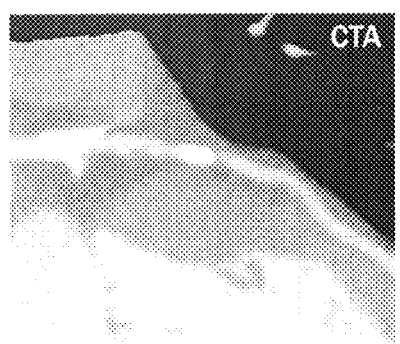 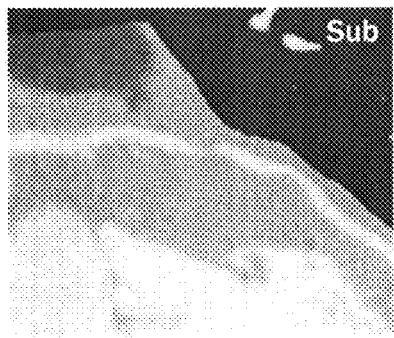
Fig. 4a  Fig. 4b

ESTIMATED LOCAL RIGID REGIONS FROM DENSE DEFORMATION IN SUBTRACTION

FIELD

Embodiments described herein relate generally to a method of, and apparatus for, registering medical image data, for example registering medical image data for use in subtraction.

BACKGROUND

Bone marrow edema (which may also be called bone bruising) is the presence of excess fluids in the bone marrow. Bone marrow edema pattern (BMEP) is a visible feature in a medical image that may indicate the presence of bone marrow edema. In some circumstances, BMEP may be associated with lytic bone lesions. Lytic bone lesions may be caused by certain bone tumors, amongst other possible causes. Visualizing BMEP can help diagnose lytic bone lesions, since relatively few bone tumors have been found to be associated with BMEP.

It is known to identify BMEP in magnetic resonance (MR) imaging. Studies have also investigated the use of computed tomography (CT) bone subtraction to identify BMEP, and compared results obtained using CT bone subtraction to results obtained using MR.

CT bone subtraction is a form of Digital Subtraction Angiography. In Digital Subtraction Angiography, a contrast agent is introduced to the vascular system of a patient. The contrast agent increases the intensity of blood as viewed in a CT image. Image data is acquired with and without the contrast agent present, and non-enhanced image data is subtracted from contrast-enhanced image data to remove features that are common to the two images (for example, bone) and to emphasize regions of contrast. In perfusion studies, multiple images may be taken at predetermined intervals to characterize the flow of contrast-enhanced blood through the vascular system.

If images that are required to be subtracted are not or may not be aligned (for example, if the patient may have moved between the first image and the second image) then registration may be used to align the sets of image data before subtraction. Registration can be used to determine a relationship between the coordinate systems of the first image data set and the second image data set, such that each anatomical location in the first image data set is mapped to the same anatomical location in the second image data set. Registration may be performed manually or automatically using known analysis techniques. Different types of registration may be used, for example rigid, affine, or non-rigid.

A rigid registration in this context may be considered to be a registration in which the coordinates of data points in one data set are subject to rotation and translation in order to register the data set to another data set. An affine registration in this context may be considered to be a registration in which the coordinates of data points in one dataset are subject to rotation, translation, scaling and/or shearing in order to register the dataset to another dataset. Thus, a rigid registration may be considered to be a particular type of affine registration.

Non-rigid registrations produce non-linear transformations, in which the coordinates of data points in one dataset are subject to flexible deformations in order to register the data set to another data set. Non-linear transformations may be defined using dense vector fields, defining an individual displacement for each voxel in a three-dimensional data set. Non-linear transformations may also be defined using other fields or functions, for example using B spline functions or thin plate spline functions.

In studies, CT images have been obtained for a set of patients, each patient having a lytic bone lesion, with the CT images being obtained from CT perfusion studies performed in a large detector CT scanner. A faint flushing of tissue may be seen while the contrast agent is introduced. In some circumstances, the effect of the contrast agent on intensity has been found to be of the order of 30 HU (Hounsfield units) and so may be difficult to distinguish.

Based on registration and subtraction of pre- and post-contrast CT image data sets using either non-rigid or rigid registrations, it has been found in some cases, in the context of CT perfusion studies on patients suffering from lytic bone lesions, that non-rigid registration gives results that may initially appear in some ways to be better than those of rigid registration, with better image quality and a reduction in subtraction artifacts when compared with rigid registration. However, non-rigid registration may result in the incorrect shrinkage or expansion of an area of BMEP (for example, associated with a tumor) after registration. Enhancement may also be reduced when compared with rigid registration. When assessing the contrast between the BMEP regions and region of bone marrow that appear normal, rigid registration may result in a higher contrast than is achieved using non-rigid registration.

BRIEF DESCRIPTION OF THE DRAWINGS

Embodiments are now described, by way of non-limiting example only, and are illustrated in the following figures, in which:

FIGS. 3a and 3b are CT subtraction images obtained from rigid and non-rigid registration respectively;

FIG. 4a is a coronary CT angiography image and FIG. 4b is a corresponding subtraction image;

DETAILED DESCRIPTION

Certain embodiments provide a medical image data processing apparatus comprising a registration unit configured to perform a non-rigid registration of a first set of medical image data and a second set of medical image data and thereby to determine a deformation field, and a region identification unit configured to identify at least one region for which the deformation field is approximately homogeneous, and, for at least part of at least one identified region, to apply a substantially homogeneous approximation of the deformation field.

Certain embodiments provide a method of medical image data processing, comprising performing a non-rigid registration of a first set of medical image data and a second set of medical image data and thereby determining a deformation field, identifying at least one region for which the deformation field is approximately homogeneous and, for at least part of at least one identified region, applying a substantially homogeneous approximation of the deformation field.

Figure 1:
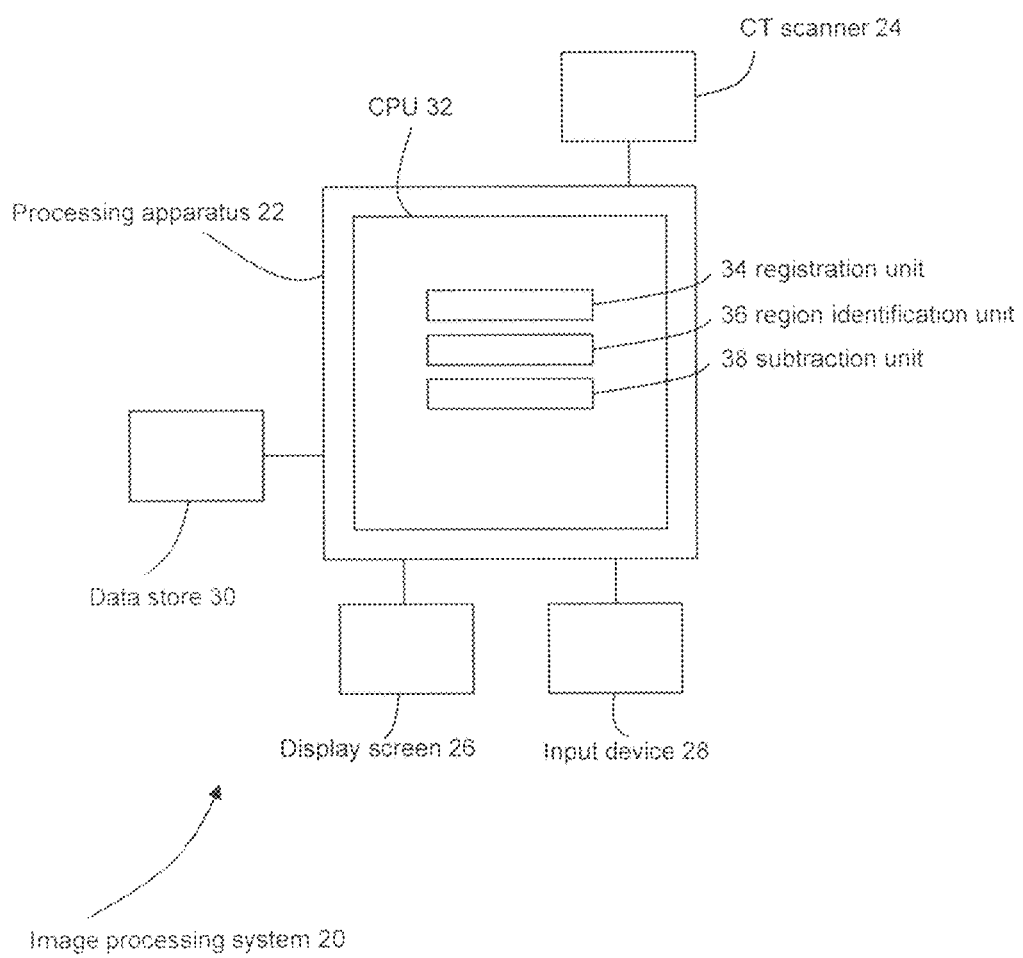
FIG. 1 is a schematic illustration of a medical image processing system according to an embodiment.

A medical image processing system 20 according to an embodiment is illustrated schematically in FIG. 1. The medical image processing system 20 comprises a processing apparatus 22. In the embodiment shown in FIG. 1, the processing apparatus 22 may comprise a personal computer (PC) or workstation, or any other suitable type of general purpose or dedicated computing device. The image processing system 20 further comprises a CT scanner 24, a display screen 26 and a user input device or devices 28, in this case a computer keyboard and mouse. The image processing system 20 also includes a data store 30.

Any suitable type of CT scanner 24 may be used that is able to perform CT measurements on a patient or other subject, for example one of the Aquilion (RTM) series of scanners produced by Toshiba Medical Systems Corporation. In other embodiments, any suitable type of scanner producing any other suitable type of image data may be used, for example MR, ultrasound, PET or SPECT data. In the present embodiment, the CT scanner produces volumetric image data. In other embodiments, two-dimensional image data may be used.

In the embodiment of FIG. 1, image data sets are received by the processing apparatus 22 from the CT scanner 24 following acquisition of scans by the scanner 24 and are stored in the data store 30 and processed by the processing apparatus 22.

In a variant of the embodiment of FIG. 1, the processing apparatus 22 receives image data sets from a remote data store (not shown). The remote data store may store a large number of different data sets obtained from many different scanners over an extended period of time together with associated patient data. For example, the data store may form part of a Picture Archiving and Communication System (PACS).

The processing apparatus 22 provides a processing resource for automatically or semi-automatically processing image data, and comprises a central processing unit (CPU) 32 that is able to load and operate a variety of software units or other software components that are configured to perform a method as described in detail below with reference to FIG. 2.

In the present embodiment, the software units include a registration unit 34 for registering sets of medical image data, a region identification unit 36 for identifying regions in which a resulting deformation field is approximately homogeneous, and a subtraction unit 38 for subtracting sets of image data.

In the present embodiment, the registration unit 34, region identification unit 36 and subtraction unit 38 are each implemented in processing apparatus 22 by means of a computer program having computer-readable instructions that are executable to perform the method of the embodiment. However, in other embodiments, the various units may be implemented as one or more ASICs (application specific integrated circuits) or FPGAs (field programmable gate arrays).

The processing apparatus 22 also includes a hard drive and other components of a PC including RAM, ROM, a data bus, an operating system including various device drivers, and hardware devices including a graphics card. Such components are not shown in FIG. 1 for clarity.

Figure 2:
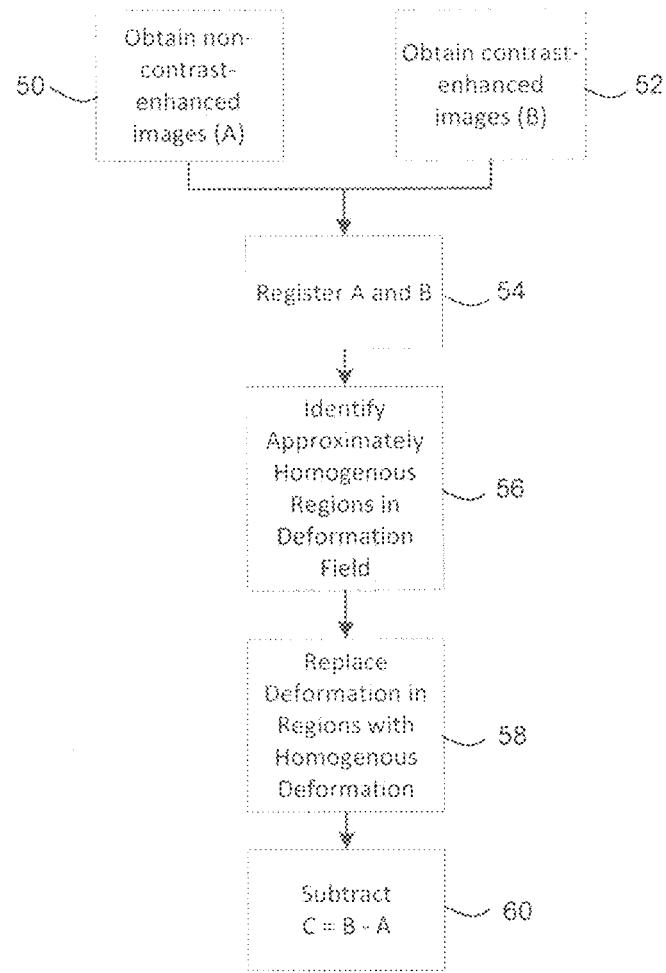
FIG. 2 is a flow chart illustrating in overview a mode of operation of the embodiment of FIG. 1.

The system of FIG. 1 is configured to perform a series of stages as illustrated in overview in the flow chart of FIG. 2.

At stage 50, the registration unit 34 receives a first set of image data and at stage 52 the registration unit 34 receives a second set of image data (stages 50 and 52 may occur simultaneously or with either stage occurring before the other). In the present embodiment, the first set of image data is a set of non-enhanced image data (which may be referred to as A) and the second set of image data is a set of contrast-enhanced image data (which may be referred to as B).

In the present embodiment, each set of image data comprises a set of volumetric CT data. In other embodiments, each set of image data may comprise a set of two-dimensional image data and/or the image data may be obtained from any suitable scan modality.

At stage 54, the registration unit 34 registers the set of non-enhanced image data (A) with the set of contrast-enhanced image data (B) using a non-rigid registration procedure. Any suitable non-rigid registration procedure may be used. In the present embodiment, the non-rigid registration procedure is similar to that reported in Piper, J et al, Objective evaluation of the correction by non-rigid registration of abdominal organ motion in low-dose 4D dynamic contrast-enhanced CT, Physics in Medicine and Biology 57(6), 1701-1715 (2012). A global non-rigid registration procedure is performed using Mutual Information as a similarity measure, and a deformation field is computed using the Crum-Hill-Hawkes scheme (William R. Crum, Derek L. G. Hill, David J. Hawkes. Information Theoretic Similarity Measures in Non-rigid Registration, Proceedings of IPMI'2003, pp. 378-387). In the present embodiment, the deformation field is a dense vector field, in which an individual displacement vector is defined for each voxel. Any other suitable non-rigid registration procedure may be used in alternative embodiments.

At stage 56, the region identification unit 36 identifies at least one region for which the deformation field determined at stage 54 is approximately homogeneous. A region for which the deformation field is approximately homogeneous may be referred to as an approximately homogeneous region. An approximately homogeneous region may be a region in which the deformation field can be sufficiently approximated by an affine transformation.

The approximately homogeneous region may be defined in the coordinate space of the non-enhanced image data or in the coordinate space of the contrast image data (the coordinate spaces being related by the non-rigid registration).

In the present embodiment, in which an individual displacement vector is associated with each voxel, an approximately homogeneous region may be a region of voxels for which the vectors for the voxels within the region are similar to within a given measure.

In some embodiments, the region identification unit 36 identifies each approximately homogeneous region by determining a variation of the deformation field within that region. Variation of the deformation field may be determined on a voxel-by-voxel basis. In some embodiments, the displacement of each individual voxel is compared with the displacement of other voxels within the approximately homogeneous region. In some embodiments, the displacement of each individual voxel is compared with an estimated approximation of the deformation field in a certain area, for example an estimated approximation of the deformation field in the approximately homogeneous region.

The variation of the deformation field may be described using any appropriate value or statistical quantity, for example by determining a variance or standard deviation.

In some embodiments, an approximately homogeneous region is a region in which the deviation of the deformation field varies by less than a threshold value. For example, an approximately homogeneous region may be a region in which the deviation in the displacement of each individual voxel varies by less than a threshold value of displacement.

In some embodiments, the region identification unit 36 identifies each approximately homogeneous region by identifying at least one region for which at least one component of the variation of the deformation field is less than a threshold value. In some embodiments, the region identification unit 36 identifies at least one region for which at least one component of the deviation (or variation) of the deformation field is substantially constant.

Any suitable method may be used to determine at least one region that is approximately homogeneous. In the present embodiment, the region identification unit 36 identifies approximately homogeneous regions of the non-rigid deformation field using a variational clustering or vector field analysis technique, for example a technique similar to k-means techniques. Examples of techniques that can be used to perform vector field analysis and variational clustering are described, for example, in McKenzie, A., Lombeyda, S., Desbrun, M., "Vector Field Analysis and Visualization through Variational Clustering," IEEE VGTC Symposium of Visualization 2005, 1-3 Jun., 2005, Leeds, UK, Eurographics 2005. In the present embodiment, the clustering technique includes the curl of the vector field to determine regions of relative rotation.

In alternative embodiments, approximately homogeneous regions of the deformation field may be determined using alternative methods. For example, a Markov Random Field may be used to estimate the approximately homogeneous regions. An embodiment in which a Markov Random Field is used is described below with reference to FIG. 5.

In the present embodiment, the number of approximately homogeneous regions is determined by the variational clustering algorithm. The number of regions is determined by how tolerant the variational clustering algorithm is to deviation from homogeneity. A very tolerant variational clustering algorithm would result in only one approximately homogeneous region. At the limit at which the tolerance is very tight, there could be one approximately homogeneous region per voxel.

The number of approximately homogeneous regions, and the extent of each approximately homogeneous region, may be different for different image data sets. For some image data sets, approximately homogeneous regions may cover only a small proportion of the coordinate space. For other image data sets, most or all of the coordinate space may be made up of regions for which the deformation field is approximately homogeneous.

In the present embodiment, a minimum region size is pre-determined and stored in the region identification unit 36. Region identification unit 36 requires approximately homogeneous regions that are identified by the variational clustering technique to meet the minimum region size. Any region that is determined to be approximately homogeneous but does not meet the minimum region size is not used as an approximately homogeneous region in subsequent stages of the process of FIG. 2.

Although in the present embodiment, the minimum region size is pre-determined, in other embodiments it may be determined in any suitable manner. For example a minimum region size may be calculated by the region identification unit 36 or may be selected by a user. In the present embodiment, the minimum region size is defined as a number of voxels. In other embodiments, a minimum region size may be described as any suitable parameter or dimension. For example, a minimum x, y, or z dimension may be determined. In alternative embodiments, no minimum region size is determined.

At stage 58, for each of the regions that has been identified as approximately homogeneous, the region identification unit 36 determines a substantially homogeneous approximation to the deformation field in that region, and replaces the non-rigid deformation in that region with the substantially homogeneous approximation.

Although in the present embodiment the identification of approximately homogeneous regions at stage 56 and the determination of a substantially homogeneous approximation at stage 58 occur as separate stages, in other embodiments, the identification of each approximately homogeneous region is part of the same stage as the determination of the substantially homogeneous approximation.

In the present embodiment, each substantially homogeneous approximation determined by the region identification unit 36 is a rigid approximation. For each region, the region identification unit 36 determines a value of rotation (for example, the value of a rotation parameter of the rigid or affine registration) from the variational clustering (for example from a value of at least one rotational parameter), and determines a translation (for example the value of a translation parameter of the rigid or affine registration) from the deformation field (for example from the value of a deformation field parameter) at the region in question. In variants of the embodiment a variation in scale is also determined, for example from an estimated divergence of the deformation field. The determined values of the rotation and translation (and scale, if used) are then combined to produce the rigid approximation for the region.

In one example of the present embodiment, the deformation field in one region is determined to be approximately homogeneous at stage 56 by using a variational clustering algorithm to determine that the vectors of the deformation field in that region have a low level of variation (for example, variation below a defined threshold). At stage 58, the region identification unit 36 determines that the deformation field in the identified region may be approximated by a translation, and determines the appropriate translation vector. The region identification unit 36 then replaces each of the deformation field vectors in the identified region with the determined translation vector.

A similar process may be applied to embodiments in which the approximation to the deformation field is more complex. Whilst in the present embodiment the region identification unit 36 determines a rigid approximation for each identified region (which may include rotation, translation and/or scaling), in other embodiments, the region identification unit 36 determines an affine approximation (which may further include shearing).

In some embodiments, the substantially homogeneous approximation is a rigid approximation, and the rigid approximation is determined using a method to approximate a local warp field as described in U.S. patent application Ser. No. 13/349,010, for example a method to approximate a local warp field using polar decomposition.

In further embodiments, any substantially homogeneous approximation may be used. For example, in some cases, the substantially homogeneous approximation may comprise a deformation field that has been constrained, for example by setting one or more parameters of the deformation field to be constant. For example, in one embodiment constraints on the deformation of the control points in a B spline may constitute the substantially homogeneous approximation.

In some embodiments, applying a substantially homogeneous approximation in a region comprises setting one or more of the parameters of the deformation field in that region to be substantially constant. In some embodiments the substantially homogeneous approximation comprises a B spline in which some parameters are fixed. In some embodiments, the substantially homogeneous approximation may be any transformation that is not entirely free-form, which may be any transformation that applies some constraint across the region.

The region identification unit 36 replaces the non-rigid deformation field for each identified region with the rigid approximation that has been determined for that region. The resulting deformation field may therefore comprise the original non-rigid deformation field for some regions (those which were not identified as approximately homogeneous) and one or more rigid approximations for regions that were identified as approximately homogeneous. In cases where there are several rigid approximations, the rigid approximations may be different from each other.

In the present embodiment, the region identification unit 36 uses a distance function to apply a smooth transition between homogeneous regions (in this embodiment, regions for which a rigid approximation has been applied) and non-homogeneous regions (regions for which the original non-rigid deformation field remains). At each boundary that separates a homogeneous region from a non-homogeneous region, a distance function is used to blend the rigid approximation with the non-rigid deformation.

Returning to the example of a region for which the rigid approximation is a translation vector, one may consider a first region for which the rigid approximation (translation) has been applied and a second, adjacent region for which the original deformation field remains. In one embodiment, for a voxel that is on the boundary between the first region and the second region, the distance function determines that the vector at that voxel is a combination of the translation vector and the non-rigid deformation vector in which the translation vector contributes 50% and the non-rigid deformation vector contributes 50%. For voxels within the first region (where the rigid approximation has been determined), the contribution of the non-rigid deformation vector decreases with distance from the boundary, such that the contribution of the non-rigid deformation vector is zero at a pre-determined distance from the boundary. For voxels within the second (non-rigid) region, the contribution of the translation vector decreases with distance from the boundary, such that the contribution of the translation vector is zero at a pre-determined distance from the boundary.

A similar method may be used to smooth a boundary between any homogeneous region and any non-homogeneous region, by combining the appropriate homogeneous approximation and non-rigid deformation over a region around the boundary. Any suitable distance function or other smoothing method may be used.

In some circumstances, one homogeneous region may border another homogeneous region, with each having a different homogeneous approximation. In such circumstances, a similar blending approach may be used, for example with voxels at the boundary having a 50% contribution from each of the vectors, and voxels near the boundary having vector contributions that are dependent on distance.

A modified deformation field is obtained which may have homogenous and non-homogenous regions with smoothed transitions between regions. (In some circumstances the entire non-rigid deformation field may have been replaced by one or more homogeneous regions. In such a case the modified deformation field will be composed of one or more homogeneous transformations.)

While in the present embodiment, each substantially homogeneous approximation is a rigid transformation, in other embodiments, each substantially homogeneous approximation may be an affine approximation or any other suitable approximation.

At stage 60, the modified deformation field is used in performing subtraction of the non-enhanced image data and the contrast image data. In the present embodiment, the subtraction unit 36 transforms the contrast image data in accordance with the modified deformation field, such that the transformed contrast image data is aligned with the non-enhanced image data. The transformation may comprise modification of the coordinates of some or all of the voxels of the contrast image data set in accordance with the modified deformation field.

By transforming the image data in accordance with the modified deformation field, image data for the regions identified as being approximately homogeneous can be transformed at least partially with the substantially homogenous approximations determined for those regions (bearing in mind that the substantially homogenous approximations may be modified at the edges of the regions by any smoothing functions that are applied).

In other embodiments, the non-enhanced image data may be transformed to the coordinate space of the contrast data such that the transformed non-enhanced image data is aligned with the contrast image data.

The resulting alignment of the image data sets may not be perfect. The accuracy of the alignment may depend on the quality of the non-rigid registration and/or the method of obtaining the substantially homogeneous approximation in each region.

The subtraction unit 38 obtains a subtraction data set (which may be referred to as C) by subtracting the non-enhanced image data set from the transformed contrast image data set. In other embodiments, the subtraction unit 38 may subtract either of the sets of image data from the other, and either or both of the data sets may be transformed before the subtraction.

In the present embodiment the non-enhanced image data set and the contrast image data set that are subtracted each comprise all of the data from the respective CT scan. In other embodiments, each of the non-enhanced image data set and the contrast image data set may comprise a subset of an image data set obtained from a CT scan.

The subtraction unit 38 renders a subtraction image from the subtraction image data set and displays the subtraction image on display screen 26. Rendering a subtraction image may comprise any method of generating a subtraction image. In some embodiments, the subtraction image is used to estimate the extent and density of BMEP in at least one region of the image. The estimation of BMEP may be performed manually, automatically, or semi-automatically.

In the present embodiment, the clinician or other user of the subtraction image may optionally view a display of the subtraction image that indicates regions for which a homogeneous approximation was applied in place of the non-rigid deformation field. The user may wish to know whether non-rigid deformation or a homogeneous approximation has been applied in a certain region, for example to determine whether features may have been deformed during registration.

In the present embodiment, the user may select a button that shades each region of the image that corresponds to an identified region in red. The viewer is thereby informed that the parts of the image that are not red were aligned using non-rigid registration, while the parts of the image that are red were aligned using, in this embodiment, a rigid approximation to the non-rigid registration in that region.

In other embodiments, the user may select the view in which the regions of rigid approximation are shown by clicking with a mouse, by a keyboard shortcut, by a toggle command, by selecting one of a plurality of views, or by any other appropriate selection method. In some embodiments, the user may select part of the subtraction image (for example by clicking and dragging a mouse) and regions of rigid approximation may be shown only for the selected part of the image and not for the rest of the image.

Although in the present embodiment, the regions for which a rigid approximation were used are indicated using red shading, in other embodiments any suitable display method may be used to indicated such regions. For example, the regions may be distinguished from non-rigid regions by applying a visual effect to the rigid regions or to the non-rigid regions, or by applying a first visual effect to rigid regions and a second, contrasting visual effect to non-rigid regions. The visual effect may comprise at least one of a brightness, a color, a texture, a shading, or an outline. In some embodiments, each rigid region may be outlined in a color. In one such embodiment, rigid regions having different rigid approximations are outlined in different colors.

Although the optional view of the regions is available in the present embodiment, in other embodiments no such view is available and only a conventional subtraction image is displayed. In alternative embodiments, the view of the regions is displayed by default and does not require user input. In further embodiments, the subtraction image may not be displayed. For example, the subtraction image data may be stored or analyzed without being displayed to a user. In some embodiments, the subtraction image data is used as an input to a further process.

In the embodiment described above with reference to FIG. 2, the deformation field for each region which was identified as approximately homogeneous is replaced by a substantially homogeneous approximation to the deformation field. By approximating the deformation field, only a single registration stage is performed. In some embodiments, identifying an approximately homogeneous region and determining a substantially homogeneous approximation to the deformation field for that region are also performed as a single stage.

However, in alternative embodiments, a rigid registration is performed for each region that is identified as approximately homogeneous and for each region, the results of the rigid registration are applied to the region in place of the non-rigid deformation field. In such embodiments, the rigid registration may be considered to result in an approximation to the non-rigid deformation field. In other embodiments, an affine registration, or any registration that is not free-form but is in some way constrained, may be used in a similar way to provide an approximation to the non-rigid deformation field.

In the embodiment of FIG. 2, regions for which the deformation field is approximately homogeneous are identified, a modified deformation field is obtained by replacing the deformation field in each identified region with a substantially homogeneous approximation to the deformation field, and transforming the contrast image data in accordance with the modified deformation field before subtraction.

Therefore in the embodiment of FIG. 2, a change is made to the deformation field before the deformation field is applied to align the image data sets.

In alternative embodiments, the contrast image data set may be transformed in accordance with the original deformation field (the deformation field obtained from the non-rigid registration), and at least one further deformation field may then be applied to the identified region. For example, in some embodiments, the further deformation field comprises the difference between the original deformation field and the modified deformation field. In alternative embodiments, a further deformation field is determined for each of the identified regions, and each of the further deformation fields is used in turn to transform the contrast image data set. In other embodiments, any change or sequence of changes may be made to the deformation field or to either set of image data that has the effect of transforming the contrast image data set using a deformation field, the deformation field for the identified regions having been replaced with substantially homogeneous approximations. Although transformation of the contrast image data set is described above, in alternative embodiments, the non-enhanced image data set may be transformed, or both image data sets may be transformed.

In the above embodiment, regions for which the deformation field is approximately homogeneous were identified using variational clustering alone. In other embodiments, other methods of identifying approximately homogeneous regions may be used. For example, other methods of clustering may be used. A combination of two or more different methods may be used.

In some embodiments, a Markov Random Field method is used to identify approximately homogeneous regions.

In one such embodiment, the basic formulation of the Ising model (Lenz, W., "Beiträge zum Verständnis der magnetischen Eigenschaften in festen Körpern", Physikalische Zeitschrift 21, 1920) is used on a graph with nodes at the voxel positions and edges between adjacent nodes. This has an energy function comprising two parts. The first part is a per-node energy, which determines independently how homogeneous a node is. The second part is a per-edge energy, which determines the likelihood that adjacent nodes are different (i.e. when a node in a homogeneous region borders one in a non-homogeneous region).

An MRF optimization is performed to give an assignment to each node. Each node is identified either as (approximately) homogenous or as non-homogeneous. In the present embodiment, the per-edge component of the MRF enforces the constraint that locally homogeneous nodes tend to clump together. In other embodiment, only a per-node component is used, and no per-edge component is used.

Figure 5:
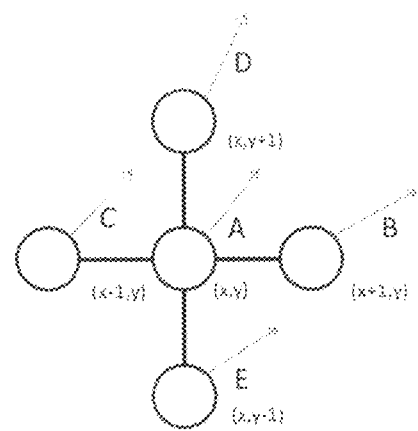
FIG. 5 is a diagram representing nodes in a Markov Random Field.

In the present embodiment, the per-node energy is computed based on warp field displacement at each node and its neighbors. FIG. 5 is a representation of five voxel positions (x+1, y), (x, y+1), (x−1, y) and (x, y−1). There is a node at each voxel position. Vectors (arrows) A to E represent the warp field displacement at the five nodes. Arrows A to E represent the warp field displacements at (x,y), (x+1, y), (x, y+1), (x−1, y) and (x, y−1) respectively.

Equations are defined on the warp field displacements that constrain the kinds of distortion allowed in the warp field.

In the present embodiment, a first set of equations is defined, which restricts scaling in each direction. The first set of equations is as follows:

$$\|(1,0)+B-A\| \approx 1$$

$$\|(1,0)+A-C\| \approx 1$$

$$\|(0,1)+D-A\| \approx 1$$

$$\|(0,1)+A-E\| \approx 1$$

If the first set of equations holds, then the warp does not substantially stretch or compress the image around the central node.

A second set of equations is defined, which restricts twisting and non-affine distortion. The second set of equations is as follows:

$$B+C \approx 2A$$

$$D+E \approx 2A$$

If the second set of equations holds, then straight lines are warped to approximately straight lines (so the warp is locally affine).

A third set of equations is defined, which restricts shearing. The third set of equations is as follows:

$$\|(1,-1)+B-D\| \approx \sqrt{2}$$

$$\|(1,-1)+E-C\| \approx \sqrt{2}$$

$$\|(1,1)+B-E\| \approx \sqrt{2}$$

$$\|(1,1)+D-C\| \approx \sqrt{2}$$

If the third set of equations holds, then the warp does not have substantial shearing.

If all three sets of equations hold, then the warp is locally rigid.

Given the first, second and third set of equations above (or similar equations), a per-node energy function can be constructed such that the per-node energy function is minimized when all of the equations in the first, second and third sets hold exactly.

In different embodiments, the equations may be weighted differently in the per-node energy function. For example the first set of equations may be weighted differently from the third set of equations if more shearing than scaling may be tolerated.

Once the per-node energy function is constructed, the per-node energy function may be applied to the warp field at each position and the resulting values may be stored.

In a final energy function, each node will contribute its respective stored value to the final energy if the node is assigned as homogeneous. If the node is assigned as non-homogeneous, it will contribute a different value to the final energy function (for example, the inverse of its respective stored value, the negation of its respective stored value, or a constant, depending on how the per-node energy is defined).

The per-edge energy function may be the same for all edges. The per-edge energy function may be higher for an edge between nodes with opposite assignments (i.e. between a homogeneous node and a non-homogeneous node) than for an edge between nodes that have the same assignment. For example, in one embodiment edges between nodes that have different assignments each contribute 1, and edges between nodes that have different assignments each contribute 0.

Having defined the per-node and per-edge energy functions, it is possible to find an assignment of homogeneous and non-homogeneous nodes that minimizes the total energy. Any suitable MRF minimizer may be used. For example, CEICM (Confidence Enhanced Iterated Conditional Modes) may be used (Hu, Y. and Dennis, T. J., "Simulated annealing and iterated conditional modes with selective and confidence enhanced update schemes", Computer-Based Medical Systems 1992).

MRF minimization may result in a domain containing a number of regions each having a high degree of local homogeneity. Regions each having a high degree of local homogeneity may be distinguished from each other by connected component labeling.

In some embodiments, the identification of approximately homogeneous regions further comprises a segmentation of some or all of the non-enhanced image data and/or some or all of the contrast image data. Segmentation is the process of identifying voxels representing a given structure in an image. For example, bones present in an image may be segmented from the rest of the image, for example by applying an intensity threshold.

It may be expected that bone is substantially rigid. Therefore bones and the tissue inside bones may not be expected to deform. It is possible to use this physical expectation in the identification of approximately homogeneous regions. If bones may be detected through segmentation, the bones may be considered to correspond to regions in which the deformation field is expected to be approximately homogeneous.

In some embodiments, a segmentation of one or both image data sets is performed, and a cluster analysis is then performed in dependence on the segmentation. In some embodiments, an initial bone segmentation of one or both image data sets is performed, and the results of the initial bone segmentation are used to provide an input to the variational clustering technique, for example to initialize a variational clustering technique. For example, in one embodiment a bone segmentation is used to obtain candidate regions in which the deformation field may be expected to be approximately homogeneous, and a variational clustering technique is used to refine the candidate regions.

In other embodiments, segmentation and cluster analysis are performed independently of one another, and the results of the segmentation are combined with the results of the cluster analysis in identifying approximately homogeneous regions. In one embodiment, bone segmentation and variational clustering are each performed independently and the results of the bone segmentation are combined with the results of the variational clustering to identify approximately homogeneous regions. The localization of the homogeneous regions may be enhanced by using a segmentation method in combination with variational clustering.

Any appropriate segmentation method may be used, for example using a threshold or using classifiers. In some embodiments, the entirety of the image data set is segmented. In other embodiments, only part of the image data set is segmented. In some embodiments, only certain anatomical features are segmented.

The result of the segmentation may be combined with the result of the variational clustering using any suitable method. Although bone segmentation is described above, segmentation of any anatomical features may be used.

In further embodiments, segmentation is used in the replacement of the deformation field in the homogeneous regions. Once approximately homogeneous regions are identified by using cluster analysis, segmentation is used to better define the regions with reference to the anatomy.

In other embodiments, segmentation may be used to determine outer limits of an area of interest. For example, if an image of the heart is being considered, segmentation may be used to find the maximum extent of the heart. The variational clustering technique may then be used to identify approximately homogeneous regions within the heart, and may not be applied to parts of the data set that do not represent the heart.

In further embodiments, any other source of information about the anatomy, for example an atlas or virtual anatomy, may be combined with the result of the variational clustering, may be used as an input to the variational clustering, or may be used in the replacement of the deformation field for the approximately homogeneous regions.

In some cases, relative movement of two or more bones (for example, as may occur at a knee or elbow) between a first image and a second image may cause subtraction artifacts to be present when a rigid registration is used to align the first image and the second image for subtraction, since a rigid registration that is correct for one bone will be incorrect for another. In some circumstances this problem may be addressed by using the method outlined above. An initial non-rigid registration is performed. A first approximately homogeneous region is identified that corresponds to the first bone, and a second approximately homogeneous region is identified that corresponds to the second bone. For each region, a homogeneous approximation (in this embodiment, a rigid approximation) to the non-rigid deformation is calculated and replaces the non-rigid deformation in that region.

It may be the case that the more accurate assessment of image features such as BMEP that is associated with rigid registration may be achieved while reducing subtraction artifacts by using a non-rigid registration for other parts of the image.

In some embodiments, applying a minimum region size as described above with reference to stage 58 may assist in obtaining regions that include large enough sections of bone to reduce artifacts while enhancing contrast. In other embodiments, a minimum region size may not be required.

By combining an overall non-rigid registration with regions of rigid (or other homogeneous) approximation, the method described above with reference to FIG. 2 may in some circumstances provide results that combine the robust motion correction, good image quality and reduced artifacts observed for non-rigid registration with the accuracy and enhancement observed for rigid registration. Resulting registered images and subtracted images may be more visually pleasing than images obtained through rigid registration, or images obtained through non-rigid registration alone. In certain cases, better estimates of BMEP density may be obtained than when non-rigid registration is used alone.

FIGS. 3*a* and 3*b* are bone perfusion subtraction images, including bone marrow regions, which provide a further demonstration of the differences between results obtained from subtraction using rigid registration (FIG. 3*a*) and results obtained from subtraction using non-rigid registration (FIG. 3*b*). Each of FIG. 3*a* and FIG. 3*b* shows an area of enhancement 10. However, the area of enhancement 10 in FIG. 3*b* is smaller than the area of enhancement 10 in FIG. 3*a*. It is possible that the method described above with reference to FIG. 2 may provide enhancement similar to that of FIG. 3*a* while using a non-rigid registration.

FIGS. 4*a* and 4*b* show an example of local rigid registration blended with a global non-rigid deformation in coronary subtraction. FIG. 4*a* is a CT angiography (contrast) image. FIG. 4*b* is a subtracted image for which a combination of global non-rigid and local rigid registration has been used. The method of FIG. 2 may provide similar results.

In FIGS. 4*a* and 4*b*, a calcification is present in the imaged vessel. The calcification is expected to be rigid. If the calcification is not aligned correctly (or deformed by non-rigid registration) then artifacts such as light or dark patches around the calcification may be present in the image. Such artifacts may, in some circumstances, prevent a clinical decision being reached regarding the degree of stenosis of the vessel in question.

Certain embodiments comprise a method in which non-rigid registration is performed producing a deformation field and regions of approximately homogeneous deformation are identified and replaced with the homogeneous approximation. In some embodiments, subtraction of the image data is performed.

In some embodiments, variational clustering is used to identify the approximately homogeneous regions. In some embodiments, a Markov Random Field is used to identify the approximately homogeneous regions.

In some embodiments, other forms of segmentation (for example, bone segmentation) are combined in the approximation of the homogeneous regions.

In some embodiments, the homogeneous regions are displayed or visualized in any relevant view so that the clinician can understand where rigid transformations have been applied.

Whilst embodiments above have been described in reference to subtraction, the registration methods described may be applied to the registration of any two or more sets of image data, whether or not subtraction is subsequently performed. The method of FIG. 2 may be used with any suitable two- or three-dimensional medical image data representing any part of the anatomy of any patient or subject. Medical may include veterinary.

Whilst particular units have been described herein, in alternative embodiments functionality of one or more of these units can be provided by a single unit, processing resource or other component, or functionality provided by a single unit can be provided by two or more units or other components in combination. Reference to a single unit encompasses multiple components providing the functionality of that unit, whether or not such components are remote from one another, and reference to multiple units encompasses a single component providing the functionality of those units.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image data processing apparatus, comprising:
   processing circuitry configured to
      perform a non-rigid registration of a first set of medical image data and a second set of medical image data, wherein each of the first set of medical image data and the second set of medical image data comprises a respective set of voxels, each voxel having an intensity value, and wherein the non-rigid registration determines a deformation field that comprises vector values representing displacements of at least one of voxels of the first set of medical image data and the corresponding voxels of the second set of medical image data according to the registration, and
      process the vector values of the deformation field to identify at least one region having a size greater than a threshold size and for which the vector values of the deformation field are approximately homogeneous, and, for at least part of said at least one identified region, to obtain a substantially homogeneous approximation of the deformation field, wherein in identifying the at least one region for which the vector values of the deformation field are approximately homogeneous, the processing circuitry is further configured to identify at least one region for which at least one component of a variation of the deformation field is less than a threshold value.

2. The medical image data processing apparatus according to claim 1, wherein the processing circuitry is further configured to perform a transformation and subtraction process, the transformation and subtraction process comprising transforming one of the first and second sets of medical image data to obtain a transformed set of image data, and subtracting the transformed set of medical image data and the other of the first and second sets of image data.

3. The medical image data processing apparatus according to claim 2, wherein in transforming the one of the first and second sets of medical image data, the processing circuitry is further configured to perform the transformation in respect of said at least one identified region at least partially in accordance with the substantially homogeneous approximation of the deformation field.

4. The medical image data processing apparatus according to claim 2, wherein in transforming the one of the first and second sets of medical image data, the processing circuitry is further configured to perform the transformation in respect of at least one other region in accordance with the deformation field for that other region.

5. The medical image data processing apparatus according to claim 2, wherein the processing circuitry is further configured to render a subtraction image.

6. The medical image data processing apparatus according to claim 5, wherein the processing circuitry is further configured to render the subtraction image such that said at least one identified region is indicated by a visual effect.

7. The medical image data processing apparatus according to claim 1, wherein the processing circuitry is further configured to, for said at least one identified region, at least partially replace the deformation field with the substantially homogeneous approximation of the deformation field to obtain a modified deformation field.

8. The medical image data processing apparatus according to claim 7, wherein the processing circuitry is further configured to transform at least one of the first set of medical image data and the second set of medical image data in accordance with the modified deformation field.

9. The medical image data processing apparatus according to claim 1, wherein the processing circuitry is further configured to perform a rigid or affine registration to obtain the substantially homogeneous approximation of the deformation field.

10. The medical image data processing apparatus according to claim 1, wherein in identifying the at least one region for which the deformation field is approximately homogeneous, the processing circuitry is further configured to perform a cluster analysis on the deformation field.

11. The medical image data processing apparatus according to claim 1, wherein in identifying the at least one region for which the at least one component of the variation of the deformation field is less than the threshold value, the processing circuitry is further configured to identify at least one region for which at least one component of the variation of the deformation field is substantially constant.

12. The medical image data processing apparatus according to claim 1, wherein the processing circuitry is configured to identify the at least one region for which the deformation field is approximately homogeneous in dependence on a segmentation of at least part of the first set of image data or of at least part of the second set of image data.

13. The medical image data processing apparatus according to claim 1, wherein in identifying the at least one region for which the deformation field is approximately homogeneous, the processing circuitry is further configured to determine at least one candidate region by performing a segmentation of at least part of the first set of image data or of at least part of the second set of image data.

14. The medical image data processing apparatus according to claim 1, wherein the processing circuitry is further configured to apply a smoothing function to one or both of the deformation field and the substantially homogeneous approximation of the deformation field to smooth a transition between the deformation field and the substantially homogeneous approximation of the deformation field.

15. The medical image data processing apparatus according to claim 1, wherein the substantially homogeneous approximation comprises at least one of a rigid approximation, an affine approximation, and an approximation in which at least one parameter of the deformation field is held constant.

16. The medical image data processing apparatus according to claim 1, wherein one of the first set of medical image data and the second set of medical image data comprises non-contrast image data and the other of the first set of medical image data and the second set of medical image data comprises contrast-enhanced image data.

17. The medical image data processing apparatus according to claim 1, wherein each of the first set of image data and the second set of image data comprises at least one of CT data and volumetric image data.

18. The medical image data processing apparatus according to claim 1, wherein each of the first set of image data and the second set of image data comprises bone marrow image data.

19. The method of medical image data processing, comprising:

performing a non-rigid registration of a first set of medical image data and a second set of medical image data, wherein each of the first set of medical image data and the second set of medical image data comprises a respective set of voxels, each voxel having an intensity value, and wherein the non-rigid registration determines a deformation field that comprises vector values representing displacements of at least one of voxels of the first set of medical image data and the corresponding voxels of the second set of medical image data according to the registration;

processing the vector values of the deformation field to identify at least one region having a size greater than a threshold size and for which the vector values of the deformation field are approximately homogeneous, wherein in identifying the at least one region for which the vector values of the deformation field are approximately homogeneous, the processing step further includes identifying at least one region for which at least one component of a variation of the deformation field is less than a threshold value; and for at least part of said at least one identified region, obtaining a substantially homogeneous approximation of the deformation field.

* * * * *